(12) United States Patent     (10) Patent No.: US 8,317,751 B2
Habeshaw et al.     (45) Date of Patent: Nov. 27, 2012

(54) INJECTION DEVICE

(75) Inventors: Rosemary Louise Habeshaw, Blinco Grove (GB); Jonathan Hogwood, Royston (GB)

(73) Assignee: Cilag GmbH International (CH)

( * ) Notice: Subject to any disclaimer, the term of this patent is extended or adjusted under 35 U.S.C. 154(b) by 58 days.

(21) Appl. No.: 11/910,544

(22) PCT Filed: Mar. 21, 2006

(86) PCT No.: PCT/GB2006/001029
§ 371 (c)(1),
(2), (4) Date: May 20, 2008

(87) PCT Pub. No.: WO2006/106293
PCT Pub. Date: Oct. 12, 2006

(65) Prior Publication Data
US 2008/0312593 A1     Dec. 18, 2008

(30) Foreign Application Priority Data
Apr. 6, 2005 (GB) .................................. 0507009.9

(51) Int. Cl.
*A61M 5/20* (2006.01)
*A61M 5/315* (2006.01)
(52) U.S. Cl. ..................................... 604/138; 604/220
(58) Field of Classification Search ................ 604/138, 604/136, 134, 187, 210, 220, 157
See application file for complete search history.

(56) References Cited

U.S. PATENT DOCUMENTS

| 1,845,036 | A | 2/1932 | Busher |
|---|---|---|---|
| 2,019,382 | A | 10/1935 | Aronson |
| 2,531,267 | A | 11/1950 | Harisch |
| 2,764,977 | A | 10/1956 | Ferguson |
| 2,828,742 | A | 4/1958 | Ashkenaz |
| 3,329,146 | A | 7/1967 | Waldman |
| 3,543,603 | A | 12/1970 | Gley, Paul R. |
| 3,656,472 | A | 4/1972 | Moura |

(Continued)

FOREIGN PATENT DOCUMENTS

CH     518102 A     1/1972

(Continued)

OTHER PUBLICATIONS

International Search Report dated Sep. 5, 2005; International Application No. PCT/GB2005/002117.

(Continued)

*Primary Examiner* — Nicholas Lucchesi
*Assistant Examiner* — Brooke M Matney (57) ABSTRACT

An injection device (110) is provided which includes a syringe (122) having a discharge nozzle (118). The syringe is movable between a retracted position in which the discharge nozzle is contained within the housing and an extended position in which the discharge nozzle extends from the housing. A trigger (114) is activatable to allow the contents of the syringe to be discharged through the discharge nozzle. There is also a releasable locking mechanism (116) which, when engaged, prevents the trigger from moving into an active position. The trigger includes a first portion (150) having a cut-out (152) which extends from a first end of the trigger in a direction substantially parallel to the first axis (101). The releasable locking mechanism includes a protrusion (154) along a second axis (181) for communicating with the first portion of the trigger when the releasable locking mechanism is engaged and for communicating with the cut-out when the releasable locking mechanism is disengaged. Such an injection device provides improved protection against accidental activation of the trigger.

7 Claims, 3 Drawing Sheets

U.S. PATENT DOCUMENTS

| | | |
|---|---|---|
| 3,702,608 A | 11/1972 | Tibbs |
| 3,742,948 A | 7/1973 | Post et al. |
| 3,797,488 A | 3/1974 | Hurschman et al. |
| 3,797,489 A | 3/1974 | Sarnoff |
| 3,880,163 A | 4/1975 | Ritterskamp |
| 4,165,739 A | 8/1979 | Doherty et al. |
| 4,180,070 A | 12/1979 | Genese |
| 4,185,628 A | 1/1980 | Kopfer |
| 4,194,505 A | 3/1980 | Schmitz |
| 4,231,368 A | 11/1980 | Becker |
| 4,299,238 A | 11/1981 | Baidwan et al. |
| 4,378,015 A | 3/1983 | Wardlaw |
| 4,394,863 A | 7/1983 | Bartner |
| 4,407,283 A | 10/1983 | Reynolds |
| 4,425,120 A | 1/1984 | Sampson et al. |
| 4,430,082 A | 2/1984 | Schwabacher |
| 4,521,237 A | 6/1985 | Logothetis |
| 4,561,856 A | 12/1985 | Cochran et al. |
| 4,636,201 A | 1/1987 | Ambrose et al. |
| 4,744,786 A | 5/1988 | Hooven et al. |
| 4,787,891 A | 11/1988 | Levin et al. |
| 4,874,383 A | 10/1989 | McNaughton |
| 4,929,232 A | 5/1990 | Sweeney et al. |
| 4,988,339 A | 1/1991 | Vadher |
| 5,009,646 A | 4/1991 | Sudo et al. |
| 5,026,349 A | 6/1991 | Schmitz et al. |
| 5,057,079 A | 10/1991 | Tiemann et al. |
| 5,092,842 A | 3/1992 | Bechtold et al. |
| 5,098,400 A | 3/1992 | Crouse et al. |
| 5,114,406 A | 5/1992 | Gabriel et al. |
| 5,122,119 A | 6/1992 | Lucas |
| 5,137,516 A | 8/1992 | Rand et al. |
| 5,141,496 A | 8/1992 | Dalto et al. |
| 5,156,599 A | 10/1992 | Ranford et al. |
| 5,176,643 A | 1/1993 | Kramer et al. |
| 5,190,526 A | 3/1993 | Murray et al. |
| 5,250,026 A | 10/1993 | Ehrlich et al. |
| 5,250,037 A | 10/1993 | Bitdinger |
| 5,263,933 A | 11/1993 | Novacek et al. |
| 5,267,963 A | 12/1993 | Bachynsky |
| 5,271,744 A | 12/1993 | Kramer et al. |
| 5,295,965 A | 3/1994 | Wilmot |
| 5,300,030 A | 4/1994 | Crossman et al. |
| 5,330,430 A | 7/1994 | Sullivan |
| 5,358,489 A | 10/1994 | Wyrick |
| 5,372,586 A | 12/1994 | Haber et al. |
| 5,391,151 A | 2/1995 | Wilmot |
| 5,405,362 A | 4/1995 | Kramer et al. |
| 5,411,488 A | 5/1995 | Pagay et al. |
| 5,425,715 A | 6/1995 | Dalling et al. |
| 5,451,210 A | 9/1995 | Kramer et al. |
| 5,478,316 A | 12/1995 | Bitdinger et al. |
| 5,480,387 A | 1/1996 | Gabriel et al. |
| 5,487,732 A | 1/1996 | Jeffrey |
| 5,489,256 A | 2/1996 | Adair |
| 5,514,097 A | 5/1996 | Knauer |
| 5,520,653 A | 5/1996 | Reilly et al. |
| 5,540,660 A | 7/1996 | Jenson et al. |
| 5,540,709 A | 7/1996 | Ramel et al. |
| 5,567,160 A | 10/1996 | Massino |
| 5,569,192 A | 10/1996 | van der Wal |
| 5,575,777 A | 11/1996 | Cover et al. |
| 5,599,302 A | 2/1997 | Lilley et al. |
| 5,599,309 A | 2/1997 | Marshall et al. |
| 5,609,577 A | 3/1997 | Haber et al. |
| 5,609,584 A | 3/1997 | Gettig et al. |
| 5,637,094 A | 6/1997 | Stewart, Jr. et al. |
| 5,645,536 A | 7/1997 | Whisson |
| 5,647,845 A | 7/1997 | Haber et al. |
| 5,665,071 A | 9/1997 | Wyrick |
| 5,681,291 A | 10/1997 | Galli |
| 5,697,908 A | 12/1997 | Imbert |
| 5,702,367 A | 12/1997 | Cover et al. |
| 5,704,911 A | 1/1998 | Parsons et al. |
| 5,709,662 A | 1/1998 | Olive et al. |
| 5,779,668 A | 7/1998 | Grabenkort |
| 5,779,677 A | 7/1998 | Frezza |
| 5,807,334 A | 9/1998 | Hodosh et al. |
| 5,817,058 A | 10/1998 | Shaw |
| 5,843,036 A | 12/1998 | Olive et al. |
| 5,868,711 A | 2/1999 | Kramer et al. |
| 5,879,327 A | 3/1999 | Moreau DeFarges et al. |
| 5,913,843 A | 6/1999 | Jentzen |
| 5,928,205 A | 7/1999 | Marshall |
| 5,954,738 A | 9/1999 | LeVaughn et al. |
| 5,957,897 A | 9/1999 | Jeffrey |
| 5,960,797 A | 10/1999 | Kramer et al. |
| 5,997,513 A | 12/1999 | Smith et al. |
| 6,015,438 A | 1/2000 | Shaw |
| 6,017,330 A | 1/2000 | Hitchins et al. |
| 6,036,675 A | 3/2000 | Thorne et al. |
| 6,045,534 A | 4/2000 | Jacobsen et al. |
| 6,068,614 A | 5/2000 | Kimber et al. |
| 6,077,247 A | 6/2000 | Marshall et al. |
| 6,083,197 A | 7/2000 | Umbaugh |
| 6,086,562 A | 7/2000 | Jacobsen et al. |
| 6,090,070 A | 7/2000 | Hager et al. |
| 6,090,078 A | 7/2000 | Erskine |
| 6,090,897 A | 7/2000 | Akasaki et al. |
| 6,099,503 A | 8/2000 | Stradella |
| 6,099,504 A | 8/2000 | Gross |
| 6,159,181 A | 12/2000 | Crossman et al. |
| 6,162,199 A | 12/2000 | Geringer |
| 6,171,276 B1 | 1/2001 | Lippe et al. |
| 6,179,812 B1 | 1/2001 | Botich et al. |
| 6,186,980 B1 | 2/2001 | Brunel |
| 6,190,363 B1 | 2/2001 | Gabbard et al. |
| 6,193,696 B1 | 2/2001 | Jansen et al. |
| 6,203,530 B1 | 3/2001 | Stewart, Sr. |
| 6,221,044 B1 | 4/2001 | Grecco |
| 6,258,068 B1 | 7/2001 | Kirchhofer et al. |
| 6,270,479 B1 | 8/2001 | Bergens et al. |
| 6,280,421 B1 | 8/2001 | Kirchhofer et al. |
| 6,293,925 B1 | 9/2001 | Safabash et al. |
| 6,371,939 B2 | 4/2002 | Bergens et al. |
| 6,371,959 B1 | 4/2002 | Trice |
| 6,387,078 B1 | 5/2002 | Gillespie, III |
| 6,391,003 B1 | 5/2002 | Lesch, Jr. |
| 6,419,658 B1 | 7/2002 | Restelli et al. |
| 6,428,528 B2 | 8/2002 | Sadowski et al. |
| 6,447,480 B1 | 9/2002 | Brunel |
| 6,454,743 B1 | 9/2002 | Weber |
| 6,454,746 B1 | 9/2002 | Bydion et al. |
| 6,461,333 B1 | 10/2002 | Frezza |
| 6,517,517 B1 | 2/2003 | Farrugia et al. |
| 6,537,252 B1 | 3/2003 | Hansen |
| 6,544,234 B1 | 4/2003 | Gabriel |
| 6,565,540 B1 | 5/2003 | Perouse et al. |
| 6,565,553 B2 | 5/2003 | Sadowski et al. |
| 6,569,115 B1 | 5/2003 | Barker et al. |
| 6,569,123 B2 | 5/2003 | Aichas et al. |
| 6,569,124 B1 | 5/2003 | Perouse |
| 6,572,581 B1 | 6/2003 | Landau |
| 6,575,939 B1 | 6/2003 | Brunel |
| 6,585,702 B1 | 7/2003 | Brunel |
| 6,589,210 B1 | 7/2003 | Rolfe |
| 6,595,957 B1 | 7/2003 | Griffiths et al. |
| 6,595,962 B1 | 7/2003 | Perthu |
| 6,607,508 B2 | 8/2003 | Knauer |
| 6,607,510 B2 | 8/2003 | Landau |
| 6,613,022 B1 | 9/2003 | Doyle |
| 6,620,137 B2 | 9/2003 | Kirchhofer et al. |
| 6,638,256 B2 | 10/2003 | Jansen et al. |
| 6,641,554 B2 | 11/2003 | Landau |
| 6,641,560 B1 | 11/2003 | Bechtold et al. |
| 6,641,565 B1 | 11/2003 | Lavi et al. |
| 6,645,170 B2 | 11/2003 | Landau |
| 6,645,181 B1 | 11/2003 | Lavi et al. |
| 6,648,835 B1 | 11/2003 | Shemesh |
| 6,648,850 B2 | 11/2003 | Landau |
| 6,656,163 B1 | 12/2003 | Marshall et al. |
| 6,673,049 B2 | 1/2004 | Hommann et al. |
| 6,676,630 B2 | 1/2004 | Landau et al. |
| 6,689,093 B2 | 2/2004 | Landau et al. |
| 6,692,469 B1 | 2/2004 | Weekes et al. |
| 6,699,220 B2 | 3/2004 | Rolfe |
| 6,740,062 B2 | 5/2004 | Hjertman |

| Patent No. | Date | Inventor |
|---|---|---|
| 6,743,199 B2 | 6/2004 | Shue et al. |
| 6,743,203 B1 | 6/2004 | Pickhard et al. |
| 6,746,429 B2 | 6/2004 | Sadowski et al. |
| 6,767,336 B1 | 7/2004 | Kaplan |
| 6,770,056 B2 | 8/2004 | Price et al. |
| 6,776,777 B2 | 8/2004 | Barrelle |
| 6,783,509 B1 | 8/2004 | Landau et al. |
| 6,793,161 B1 | 9/2004 | Fujia et al. |
| 6,796,967 B2 | 9/2004 | Jensen |
| 6,811,548 B2 | 11/2004 | Jeffrey |
| 6,846,303 B2 | 1/2005 | Eakins et al. |
| 6,890,319 B1 | 5/2005 | Crocker |
| 6,899,698 B2 | 5/2005 | Sams |
| 6,932,793 B1 | 8/2005 | Marshall et al. |
| 6,939,319 B1 | 9/2005 | Anstead et al. |
| 6,979,316 B1 | 12/2005 | Rubin et al. |
| 7,066,907 B2 | 6/2006 | Crossman et al. |
| 7,097,634 B2 | 8/2006 | Gilbert |
| 7,118,553 B2 | 10/2006 | Scherer |
| 7,156,823 B2 | 1/2007 | Landau et al. |
| 7,744,561 B2 | 6/2010 | Stamp |
| 2001/0005781 A1 | 6/2001 | Bergens et al. |
| 2001/0021828 A1 | 9/2001 | Fischer et al. |
| 2001/0037087 A1 | 11/2001 | Knauer |
| 2001/0037089 A1 | 11/2001 | Domici, Jr. |
| 2001/0049496 A1 | 12/2001 | Kirchhofer et al. |
| 2002/0072709 A1 | 6/2002 | Sadowski et al. |
| 2002/0095120 A1 | 7/2002 | Larsen et al. |
| 2002/0151839 A1 | 10/2002 | Landau |
| 2002/0161334 A1 | 10/2002 | Castellano et al. |
| 2002/0173752 A1 | 11/2002 | Polzin |
| 2002/0183690 A1 | 12/2002 | Arnisolle |
| 2003/0036679 A1 | 2/2003 | Kortenbach |
| 2003/0036725 A1 | 2/2003 | Lavi et al. |
| 2003/0050609 A1 | 3/2003 | Sams |
| 2003/0060773 A1 | 3/2003 | Nguyen |
| 2003/0065286 A1 | 4/2003 | Landau |
| 2003/0078546 A1 | 4/2003 | Jensen |
| 2003/0088207 A1 | 5/2003 | Rogatchev et al. |
| 2003/0088216 A1 | 5/2003 | Py |
| 2003/0093030 A1 | 5/2003 | Landau |
| 2003/0093035 A1 | 5/2003 | Mohammed |
| 2003/0093036 A1 | 5/2003 | Crossman et al. |
| 2003/0105430 A1 | 6/2003 | Lavi et al. |
| 2003/0109833 A1 | 6/2003 | Sahpe |
| 2003/0120212 A1 | 6/2003 | Dedig et al. |
| 2003/0120222 A1 | 6/2003 | Vaillancourt |
| 2003/0121815 A1 | 7/2003 | Bergeron et al. |
| 2003/0135157 A1 | 7/2003 | Saulenas et al. |
| 2003/0181859 A1 | 9/2003 | Brunel |
| 2003/0184973 A1 | 10/2003 | Nagata et al. |
| 2003/0196928 A1 | 10/2003 | Parsons |
| 2003/0199814 A1 | 10/2003 | Parsons et al. |
| 2003/0208164 A1 | 11/2003 | Botich et al. |
| 2003/0212362 A1 | 11/2003 | Roser |
| 2003/0212370 A1 | 11/2003 | Barrelle |
| 2003/0212380 A1 | 11/2003 | Barrelle |
| 2003/0225368 A1 | 12/2003 | Landau et al. |
| 2003/0233070 A1 | 12/2003 | De La serna et al. |
| 2003/0236502 A1 | 12/2003 | De La Serna et al. |
| 2003/0236504 A1 | 12/2003 | Chen |
| 2004/0015134 A1 | 1/2004 | Lavi et al. |
| 2004/0019326 A1 | 1/2004 | Gilbert et al. |
| 2004/0039336 A1 | 2/2004 | Amark et al. |
| 2004/0039366 A1 | 2/2004 | MacLeod |
| 2004/0069044 A1 | 4/2004 | Lavi et al. |
| 2004/0087897 A1 | 5/2004 | Hjertman |
| 2004/0102740 A1 | 5/2004 | Meloul |
| 2004/0111054 A1 | 6/2004 | Landau et al. |
| 2004/0111057 A1 | 6/2004 | Wilkinson |
| 2004/0133159 A1 | 7/2004 | Haider et al. |
| 2004/0138618 A1 | 7/2004 | Mazzoni |
| 2004/0143224 A1 | 7/2004 | Field et al. |
| 2004/0153033 A1 | 8/2004 | Mazzoni |
| 2004/0225262 A1 | 11/2004 | Fathallah et al. |
| 2004/0243065 A1 | 12/2004 | McConnell et al. |
| 2005/0011780 A1 | 1/2005 | Simon et al. |
| 2005/0020979 A1 | 1/2005 | Westbye et al. |
| 2005/0027255 A1 | 2/2005 | Lavi et al. |
| 2005/0033234 A1 | 2/2005 | Sadowski et al. |
| 2005/0035029 A1 | 2/2005 | Grob |
| 2005/0040716 A1 | 2/2005 | Schmid et al. |
| 2005/0049550 A1 | 3/2005 | Kirchhofer et al. |
| 2005/0049561 A1 | 3/2005 | Hommann et al. |
| 2005/0075608 A1 | 4/2005 | Holdgate et al. |
| 2005/0085776 A1 | 4/2005 | Hommann et al. |
| 2005/0090782 A1 | 4/2005 | Marshall et al. |
| 2005/0097238 A1 | 5/2005 | Oomori et al. |
| 2005/0101919 A1 | 5/2005 | Brunnberg |
| 2005/0124940 A1 | 6/2005 | Martin et al. |
| 2005/0125019 A1 | 6/2005 | Kudna et al. |
| 2005/0137523 A1 | 6/2005 | Wyatt et al. |
| 2005/0203466 A1 | 9/2005 | Hommann et al. |
| 2005/0215941 A1 | 9/2005 | Bernard et al. |
| 2005/0215951 A1 | 9/2005 | Saulenas et al. |
| 2005/0222539 A1 | 10/2005 | Gonzales et al. |
| 2005/0261633 A1 | 11/2005 | Khalaj |
| 2005/0261634 A1 | 11/2005 | Karlsson |
| 2005/0273054 A1 | 12/2005 | Asch |
| 2005/0273055 A1 | 12/2005 | Harrison et al. |
| 2005/0277885 A1 | 12/2005 | Scherer |
| 2005/0277886 A1 | 12/2005 | Hommann et al. |
| 2005/0277896 A1 | 12/2005 | Messerli et al. |
| 2005/0288633 A1 | 12/2005 | Jeffrey |
| 2006/0030819 A1 | 2/2006 | Young et al. |
| 2006/0036216 A1 | 2/2006 | Rimlinger et al. |
| 2006/0036217 A1 | 2/2006 | Doyle |
| 2006/0069345 A1 | 3/2006 | Anderson et al. |
| 2006/0069348 A1 | 3/2006 | Parker et al. |
| 2006/0069350 A1 | 3/2006 | Buenger et al. |
| 2006/0079834 A1 | 4/2006 | Tennican et al. |
| 2006/0100588 A1 | 5/2006 | Brunnberg et al. |
| 2006/0106295 A1 | 5/2006 | Jais et al. |
| 2006/0161111 A1 | 7/2006 | Potter et al. |
| 2006/0178631 A1 | 8/2006 | Gillespie et al. |
| 2006/0178642 A1 | 8/2006 | Gillespie et al. |
| 2006/0184137 A1 | 8/2006 | Reynolds |
| 2006/0224124 A1 | 10/2006 | Scherer |
| 2006/0258986 A1 | 11/2006 | Hunter et al. |
| 2006/0258990 A1 | 11/2006 | Weber |
| 2006/0270986 A1 | 11/2006 | Hommann et al. |
| 2007/0027430 A1 | 2/2007 | Hommann |
| 2007/0078382 A1 | 4/2007 | Hommann et al. |
| 2007/0142787 A1 | 6/2007 | Scherer |
| 2008/0312606 A1 | 12/2008 | Harrison et al. |
| 2009/0054849 A1 | 2/2009 | Burnell et al. |
| 2009/0088688 A1 | 4/2009 | Timothy Donald et al. |
| 2010/0016793 A1 | 1/2010 | Jennings et al. |

FOREIGN PATENT DOCUMENTS

| | | |
|---|---|---|
| CN | 2059579 U | 7/1990 |
| CN | 1190599 A | 8/1998 |
| CN | 1541121 A | 10/2004 |
| CN | 1550240 A | 12/2004 |
| DD | 229932 A1 | 11/1985 |
| DE | 902776 C | 1/1954 |
| DE | 3604826 A1 | 10/1986 |
| DE | 4428467 A1 | 2/1996 |
| DE | 29513214 U1 | 1/1997 |
| DE | 69506521 T2 | 6/1999 |
| DE | 10137962 A1 | 2/2003 |
| DE | 10207276 A1 | 9/2003 |
| DE | 20311996 U1 | 10/2003 |
| EP | 0111724 B1 | 11/1983 |
| EP | 0096314 A2 | 12/1983 |
| EP | 0144625 A2 | 6/1985 |
| EP | 0240787 A2 | 3/1987 |
| EP | 0516473 A | 12/1992 |
| EP | 0331452 A2 | 8/1993 |
| EP | 0585626 A1 | 3/1994 |
| EP | 0389938 B1 | 5/1994 |
| EP | 0482677 B1 | 4/1998 |
| EP | 0602883 B1 | 7/1998 |
| EP | 0857491 A1 | 8/1998 |
| EP | 0824922 B1 | 4/2002 |
| EP | 1260241 A1 | 11/2002 |
| EP | 0824923 B1 | 7/2003 |
| EP | 1228777 B1 | 10/2003 |

| | | | | | | |
|---|---|---|---|---|---|---|
| EP | 0991441 B1 | 12/2003 | | JP | 2004-33737 A | 8/2005 |
| EP | 1166809 B1 | 3/2004 | | NZ | 573171 A | 11/2010 |
| EP | 0666084 B1 | 4/2004 | | NZ | 573350 A | 12/2010 |
| EP | 0941133 B1 | 4/2004 | | WO | 88/08725 | 11/1988 |
| EP | 1124601 B1 | 12/2004 | | WO | 88/10129 A1 | 12/1988 |
| EP | 1364667 B1 | 4/2005 | | WO | 98/10129 A1 | 12/1988 |
| EP | 1208858 B1 | 6/2006 | | WO | 92/19296 A | 11/1992 |
| EP | 1755710 A1 | 2/2007 | | WO | 93/02186 A1 | 2/1993 |
| EP | 1586341 B1 | 1/2008 | | WO | 93/21986 A2 | 11/1993 |
| EP | 1932558 A1 | 6/2008 | | WO | 93/23098 A1 | 11/1993 |
| EP | 2023980 A1 | 2/2009 | | WO | 94/04207 A1 | 3/1994 |
| EP | 2129414 A1 | 12/2009 | | WO | 94/07554 A1 | 4/1994 |
| EP | 1755706 B1 | 3/2010 | | WO | 94/11041 | 5/1994 |
| EP | 1928523 B1 | 7/2010 | | WO | 94/13342 A1 | 6/1994 |
| EP | 1518575 B1 | 11/2010 | | WO | 94/21316 A1 | 9/1994 |
| FR | 1014881 A | 8/1952 | | WO | 94/22511 A1 | 10/1994 |
| FR | 1169935 A | 1/1959 | | WO | 95/04562 A1 | 2/1995 |
| FR | 1538565 A | 9/1968 | | WO | 95/29720 A1 | 11/1995 |
| FR | 2506161 A1 | 11/1982 | | WO | 95/31235 A1 | 11/1995 |
| FR | 2629706 A | 10/1989 | | WO | 95/35126 A1 | 12/1995 |
| FR | 2654938 A1 | 5/1991 | | WO | WO 95/35126 | 12/1995 |
| FR | 2665079 A1 | 1/1992 | | WO | 96/30065 A1 | 10/1996 |
| FR | 2717086 A1 | 9/1995 | | WO | 97/10865 A1 | 3/1997 |
| FR | 2741810 A1 | 6/1997 | | WO | 97/13538 A1 | 4/1997 |
| FR | 2861310 A1 | 4/2005 | | WO | 97/48430 A1 | 12/1997 |
| GB | 143084 | 5/1920 | | WO | 98/11927 A1 | 3/1998 |
| GB | 0412054 | 6/1934 | | WO | 99/03529 A2 | 1/1999 |
| GB | 728248 | 4/1955 | | WO | 99/10030 A2 | 3/1999 |
| GB | 909898 | 11/1962 | | WO | 99/22789 A1 | 5/1999 |
| GB | 1263355 | 2/1972 | | WO | 99/37343 A | 7/1999 |
| GB | 1311937 A | 3/1973 | | WO | 99/53979 A1 | 10/1999 |
| GB | 1514725 | 6/1978 | | WO | 99/59658 A1 | 11/1999 |
| GB | 2338033 A | 12/1999 | | WO | 00/06227 A1 | 2/2000 |
| GB | 2388033 A | 11/2003 | | WO | 00/07539 A1 | 2/2000 |
| GB | 2396298 A | 6/2004 | | WO | 00/13723 A2 | 3/2000 |
| GB | 2396816 A | 7/2004 | | WO | 00/24441 A1 | 5/2000 |
| GB | 2397767 A | 8/2004 | | WO | 00/35516 | 6/2000 |
| GB | 2414398 A | 11/2005 | | WO | 00/50107 A1 | 8/2000 |
| GB | 2414399 A | 11/2005 | | WO | 00/64515 A1 | 11/2000 |
| GB | 2414400 A | 11/2005 | | WO | 00/69488 A2 | 11/2000 |
| GB | 2414401 A | 11/2005 | | WO | 01/05456 A1 | 1/2001 |
| GB | 2414402 A | 11/2005 | | WO | 01/49347 A1 | 7/2001 |
| GB | 2414403 A | 11/2005 | | WO | 01/76666 A1 | 10/2001 |
| GB | 2424835 A | 10/2006 | | WO | 01/77384 A2 | 10/2001 |
| GB | 2424836 A | 10/2006 | | WO | 01/87384 A2 | 11/2001 |
| GB | 2424838 A | 10/2006 | | WO | 02/11799 A1 | 2/2002 |
| GB | 2433035 A | 6/2007 | | WO | 02/47746 A1 | 6/2002 |
| GB | 2437922 A | 11/2007 | | WO | 02/056947 A1 | 7/2002 |
| GB | 2438591 A | 12/2007 | | WO | 03/013632 A2 | 2/2003 |
| GB | 2446778 A | 8/2008 | | WO | 03/015853 A1 | 2/2003 |
| JP | 59-115053 A | 7/1984 | | WO | 03/039633 A2 | 5/2003 |
| JP | 2-185261 A | 7/1990 | | WO | 03/041768 A | 5/2003 |
| JP | 2-502971 T | 9/1990 | | WO | 03/051434 A2 | 6/2003 |
| JP | 11-501549 T | 2/1992 | | WO | WO 03/047663 | 6/2003 |
| JP | 5-161712 A | 6/1993 | | WO | 03/066141 A1 | 8/2003 |
| JP | 6-209996 A | 8/1994 | | WO | 03/092771 | 11/2003 |
| JP | 6-508773 T | 10/1994 | | WO | 03/097133 | 11/2003 |
| JP | 6-327770 A | 11/1994 | | WO | 03/099358 A2 | 12/2003 |
| JP | 7-222799 A | 8/1995 | | WO | 2004/007554 A1 | 1/2004 |
| JP | 8-502180 T | 3/1996 | | WO | 2004/011065 A1 | 2/2004 |
| JP | 8-504354 T | 5/1996 | | WO | 2004/030732 A2 | 4/2004 |
| JP | 9-225029 A | 9/1997 | | WO | 2004/035117 A2 | 4/2004 |
| JP | 10-504474 T | 5/1998 | | WO | 2004/047890 A1 | 6/2004 |
| JP | 10-507935 A | 8/1998 | | WO | 2004/047891 A1 | 6/2004 |
| JP | 11-503637 T | 3/1999 | | WO | 2004/047892 A | 6/2004 |
| JP | 11-504536 T | 4/1999 | | WO | 2004/054644 A1 | 7/2004 |
| JP | 11-164887 T | 6/1999 | | WO | 2004/054645 A3 | 7/2004 |
| JP | 11-512332 T | 10/1999 | | WO | 2004/087242 A1 | 10/2004 |
| JP | 2000-510021 T | 8/2000 | | WO | 2004/108194 A1 | 12/2004 |
| JP | 2002-500933 T | 1/2002 | | WO | 2005/009515 A1 | 2/2005 |
| JP | 2002-095749 A | 4/2002 | | WO | 2005/023341 A1 | 3/2005 |
| JP | 2002-513547 T | 5/2002 | | WO | 2005/025636 A3 | 3/2005 |
| JP | 2002-526175 A | 8/2002 | | WO | 2005/030301 A1 | 4/2005 |
| JP | 2002-528182 T | 9/2002 | | WO | 2005/035028 A1 | 4/2005 |
| JP | 2002-532161 T | 10/2002 | | WO | 2005/044345 A | 5/2005 |
| JP | 2003-511105 T | 3/2003 | | WO | 2005/044347 A1 | 5/2005 |
| JP | 2003-532500 T | 11/2003 | | WO | 2005/058396 A1 | 6/2005 |
| JP | 2003-533288 A | 11/2003 | | WO | 2005/070481 A1 | 8/2005 |
| JP | 2004-533282 T | 11/2004 | | WO | 2005/082438 A1 | 9/2005 |

| | | | |
|---|---|---|---|
| WO | 2005/097238 A3 | 10/2005 |
| WO | 2005/115507 A1 | 12/2005 |
| WO | 2005/115508 A1 | 12/2005 |
| WO | 2005/115509 A1 | 12/2005 |
| WO | 2005/115512 A1 | 12/2005 |
| WO | 2005/115513 A1 | 12/2005 |
| WO | 2005/115514 A1 | 12/2005 |
| WO | 2005/120607 A2 | 12/2005 |
| WO | WO 2005/115510 | 12/2005 |
| WO | 2006/044236 A2 | 4/2006 |
| WO | 2006/050304 A1 | 5/2006 |
| WO | 2006/062788 A2 | 6/2006 |
| WO | 2006/063015 A2 | 6/2006 |
| WO | 2006/063124 A2 | 6/2006 |
| WO | 2006/088513 A1 | 8/2006 |
| WO | 2006/088630 A2 | 8/2006 |
| WO | 2006/099441 A2 | 9/2006 |
| WO | 2006/106290 A1 | 10/2006 |
| WO | 2006/106291 A1 | 10/2006 |
| WO | 2006/106292 A1 | 10/2006 |
| WO | 2006/106293 A1 | 10/2006 |
| WO | 2006/106294 A | 10/2006 |
| WO | 2006/106295 A1 | 10/2006 |
| WO | 2006/118616 A1 | 11/2006 |
| WO | 2006/129196 A1 | 12/2006 |
| WO | 2007/027204 A2 | 3/2007 |
| WO | 2007/036676 A1 | 4/2007 |
| WO | 2007/047200 A1 | 4/2007 |
| WO | 2007/051330 A1 | 5/2007 |
| WO | 2007/066152 A | 6/2007 |
| WO | 2007/122193 A1 | 11/2007 |
| WO | 2007/131013 A | 11/2007 |
| WO | 2007/138299 A1 | 12/2007 |
| WO | 2008/047372 A2 | 4/2008 |
| WO | 2008/075033 A | 6/2008 |
| WO | 2008/093063 A2 | 8/2008 |

OTHER PUBLICATIONS

International Search Report dated May 30, 2006; International Application No. PCT/GB2005/003725.
International Search Report dated Sep. 9, 2005; International Application No. PCT/GB2005/002126.
Australian Search Report dated Dec. 6, 2007; Application No. SG 200608164-0.
International Search Report dated Sep. 5, 2005; International Application No. PCT/GB2005/002131.
Austrian Search Report dated Jan. 22, 2006; Application No. 200608166-5.
International Search Report dated Sep. 9, 2005; International Application No. PCT/GB2005/002120.
International Search Report dated Sep. 6, 2005; International Application No. PCT/GB2005/002108.
European Search Report dated Apr. 23, 2007; Application No. 06077332.2.
International Search Report dated Sep. 5, 2005; International Application No. PCT/GB2005/002105.
Singapore Search Report dated Feb. 26, 2008; Application No. 200608070-9.
International Search Report dated Sep. 5, 2005; International Application No. PCT/GB2005/002116.
International Search Report dated Sep. 5, 2005; International Application No. PCT/GB2005/002128.
Australian Search Report dated Dec. 11, 2007; Application No. 200608165-7.
International Search Report dated May 23, 2006; International Application No. PCT/GB2006/001017.
International Search Report dated May 29, 2006; International Application No. PCT/GB2006/001018.
International Search Report dated Jun. 2, 2006; International Application No. PCT/GB2006/001030.
International Search Report dated Jun. 1, 2006; International Application No. PCT/GB2006/001029.
International Search Report dated Sep. 9, 2005 International Application No. PCT/GB2005/002135.
International Search Report dated May 30, 2006; International Application No. PCT/GB2006/001031.
International Search Report dated Jun. 27, 2006; International Application No. PCT/GB2006/001023.
International Search Report dated Feb. 27, 2007; International Application No. PCT/1B2006/002792.
European Search Report dated Feb. 1, 2006; Application No. 05255298.1.
Great Britain Search Report dated Sep. 22, 2006; Application No. GB0610860.9.
International Search Report dated Aug. 22, 2007; International Application No. PCT/GB2007/001992.
International Search Report dated Sep. 4, 2007; International Application No. PCT/GB2007/002002.
Great Britain Search Report dated Sep. 28, 2006; Application No. GB0610859.1.
International Search Report dated Aug. 22, 2007; International Application No. PCT/GB2007/001973.
International Search Report dated Feb. 26, 2008; International Application No. PCT/GB2007/004335.
International Search Report dated Sep. 13, 2007; International Application No. PCT/GB2007/001999.
International Search Report dated Aug. 28, 2007; International Application No. PCT/GB2007/001969.
International Search Report dated Oct. 10, 2008; International Application No. PCT/GB2008/002578.
Great Britain Search Report dated Nov. 12, 2007; Application No. GB0715460.2.
International Search Report dated Oct. 14, 2008; International Application No. PCT/GB2008/002580.
Great Britain Search Report dated Nov. 12, 2007; Application No. GB0715459.4.
International Search Report dated Nov. 27, 2008; International Application No. PCT/GB2008/002579.
Great Britain Search Report dated Nov. 12, 2007; Application No. GB0715461.0.
International Search Report dated Oct. 10, 2008; International Application No. PCT/GB2008/002573.
Great Britain Search Report dated Nov. 12, 2007; Application No. GB0715456.0.
International Search Report dated Oct. 10, 2008; International Application No. PCT/GB2008/002583.
Great Britain Search Report dated Nov. 12, 2007; Application No. GB0715457.8.
International Search Report dated Sep. 30, 2009; International Application No. PCT/GB2009/001447.
Great Britain Search Report dated Sep. 25, 2008; Application No. GB0811348.2.
International Search Report dated Oct. 2, 2009; International Application No. PCT/GB2009/001448.
Great Britain Search Report dated Sep. 25, 2008; Application No. GB0811346.6.
International Search Report dated Oct. 5, 2009; International Application No. PCT/GB2009/001451.
Great Britain Search Report dated Sep. 25, 2008; Application No. GB0811347.4.
International Search Report dated Oct. 6, 2009; International Application No. PCT/GB2009/001453.
Great Britain Search Report dated Sep. 25, 2008; Application No. GB0811345.8.
International Search Report dated Oct. 5, 2009; International Application No. PCT/GB2009/001445.
Great Britain Search Report dated Sep. 25, 2008; Application No. GB0811349.0.
International Search Report dated Jan. 22, 2010; International Application No. PCT/GB2009/001446.
Great Britain Search Report dated Sep. 25, 2008; Application No. GB0811343.3.
International Search Report dated Jan. 12, 2008; International Application No. PCT/GB2008/002475.
Great Britain Search Report dated Nov. 16, 2007; Application No. GB0716774.5.

INJECTION DEVICE

FIELD OF THE INVENTION

The present invention relates to an injection device of the type that receives a syringe, extends it, discharges its contents and then retracts it automatically.

BACKGROUND OF THE INVENTION

Previously known injection devices are shown in WO 95/35126 and EP-A-0 516 473 and tend to employ a drive spring and a trigger that, when activated, causes the drive spring to act on the syringe when a releasable locking mechanism is also engaged.

Generally, the trigger is rotatable about an axis so that when it is depressed at a first end, a second end (which normally engages the drive spring) is also rotated, thereby releasing the drive spring, extending the syringe and discharging its contents. The trigger comprises a protrusion which is engageable with a cut-out on the releasable locking mechanism when the releasable locking mechanism is engaged, thereby allowing the trigger to be activated. When the releasable locking mechanism is not engaged, the protrusion abuts a portion of the releasable locking mechanism preventing rotation of the trigger and release of the drive spring. This way, accidental activation of the trigger can be prevented.

A problem with an injection device of this type is that the protrusion on the trigger flexes when a force is applied to the trigger and the releasable locking mechanism is not engaged. A strong force applied to the trigger can cause enough flex in the protrusion that the end of the protrusion can engage the cut-out on the releasable locking mechanism, thereby allowing the trigger to be activated even when the releasable locking mechanism has not been engaged.

SUMMARY OF THE INVENTION

The injection device of the present invention is designed to deal with this and other problems.

In view of the foregoing and in accordance with a first aspect of the invention, there is provided an injection device comprising:

- a housing defining a first axis and adapted to receive a syringe having a discharge nozzle so that the syringe is movable between a retracted position in which the discharge nozzle is contained within the housing and an extended position in which the discharge nozzle extends from the housing through an exit aperture;
- a drive that is acted upon and in turn acts upon the syringe;
- a trigger movable from a rest position, in which it causes the drive to be retained, to an active position, in which it no longer causes the drive to be so retained, thus allowing the contents of the syringe to be discharged through the discharge nozzle; and
- a releasable locking mechanism movable from a first position in which the trigger is prevented from moving into its active position to a second position in which the trigger can be moved into its active position,
- wherein the trigger includes a first portion having a cut-out therein, the first portion extending from a first end of the trigger in a direction substantially parallel to the first axis; and the releasable locking mechanism includes a protrusion along a second axis for communicating with the first portion of the trigger when the releasable locking mechanism is in its first position and for communicating with the cut-out when the releasable locking mechanism is in its second position.

Thus, when a force is applied to the trigger when the locking mechanism is in its first position (i.e. engaged), the first portion of the trigger and the protrusion both flex in such a way that the protrusion is forced away from the cut-out, thereby decreasing the risk of accidental activation of the trigger.

In one embodiment of the invention, the protrusion comprises a first ridge adapted to communicate with an edge of the cut-out when the releasable locking mechanism is in its second position and the trigger is in its active position, thereby preventing movement of the trigger from its active position to its rest position.

In addition, the trigger may further include a second portion which extends into the cut-out from the first portion of the trigger and which is arranged to communicate with the ridge when the releasable locking mechanism is in its second position and the trigger is in its active position.

Accordingly, the trigger can be maintained in a rotated position following activation, thereby serving to indicate that the injection device has been used.

Preferably, the releasable locking mechanism comprises biasing means arranged to bias the protrusion against the second portion.

Advantageously, the first portion of the trigger comprises a second ridge positioned on the first portion such that the protrusion is located between the cut-out and the second ridge when the trigger is in its rest position such that the second ridge communicates with the protrusion if an attempt is made to move the trigger from its rest position.

The second ridge prevents the first portion of the trigger and the protrusion flexing in such a way that the end of the protrusion extends beyond the end of the first portion which would result in the trigger being able to rotate.

The protrusion may comprise a sloped surface which is angled with respect to the second axis, thereby ensuring that the protrusion enters the cut-out smoothly when the locking mechanism is disengaged.

Preferably, the first axis and second axis are perpendicular to each other which ensures that the protrusion and first portion are optimally arranged to ensure that the protrusion enters the cut-out when the locking mechanism is disengaged, but also means that the protrusion and first portion will flex in such a way to avoid accidental activation of the trigger when the release mechanism is engaged.

BRIEF DESCRIPTION OF THE DRAWINGS

The invention will now be described by way of example with reference to the accompanying drawings, in which.

DETAILED DESCRIPTION OF THE DRAWINGS

FIGS. 1 to 4 show an injection device 110 according to a first embodiment of the present invention. The injection device 110 has an injection device housing 112 and a longitudinal axis 101.

Figure 1:
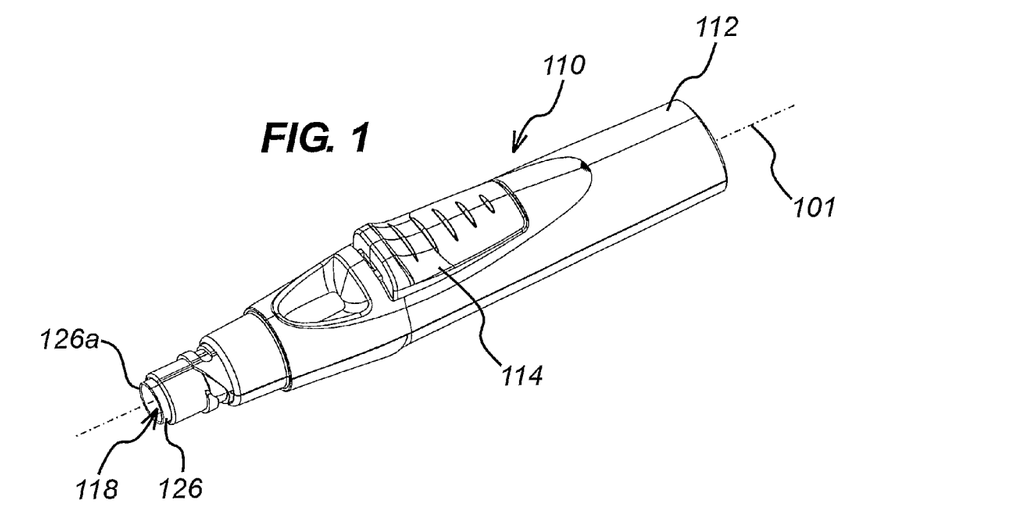
FIG. 1 shows a perspective view of an injection device according to the present invention.
Figure 2:
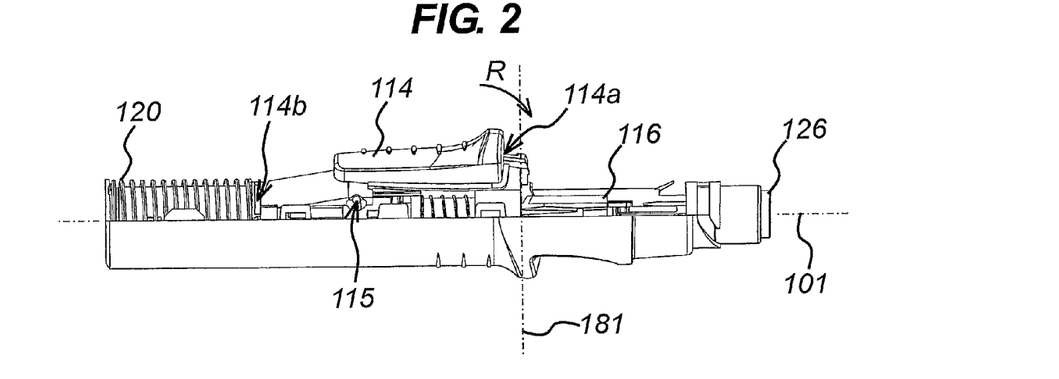
FIG. 2 shows a side view of the injection device of FIG. 1 with an upper section of its housing not shown.
Figure 3:
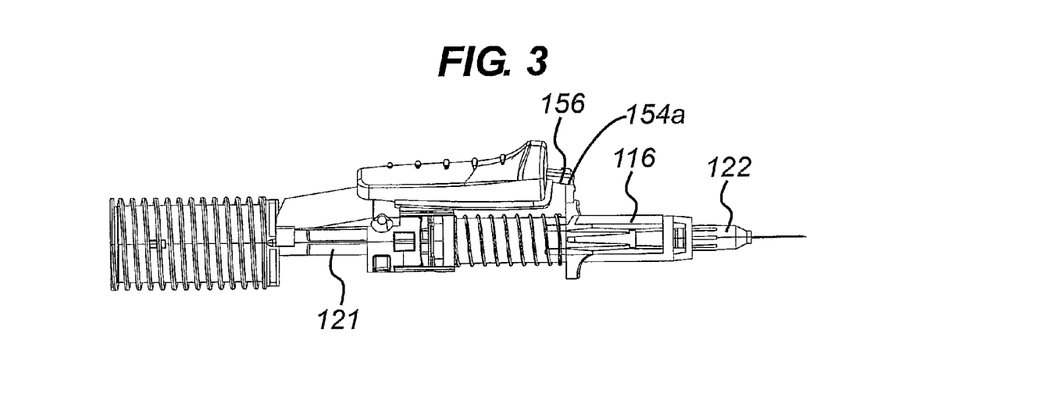
FIG. 3 shows a side view of the injection device of FIG. 2 with further components not shown.
Figure 4:
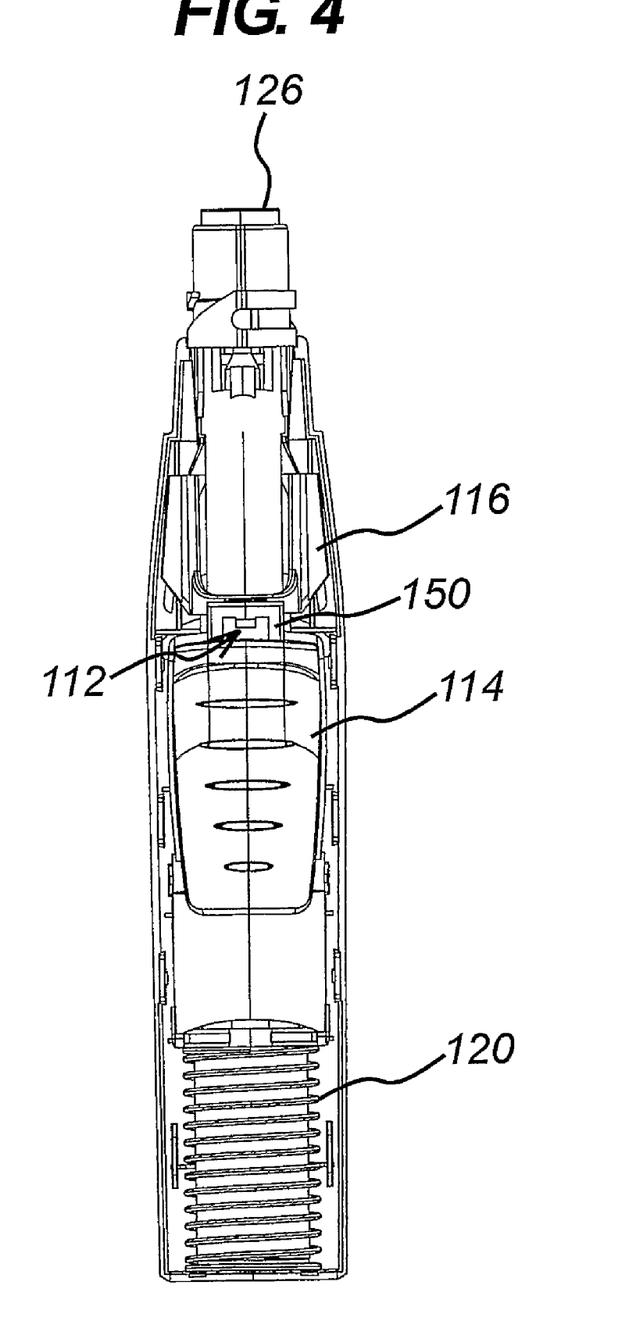
FIG. 4 shows a top plan view of the injection device of FIG. 2.

A syringe 122 is contained in the housing 112. The injection device 110 comprises trigger 114 and a releasable locking mechanism 116. The trigger 114 has a first end 114a and a second end 114b. The trigger 114 is rotatable about a pivot 115 from a rest position (as shown in FIG. 2) to an active position. The second end 114b of the trigger 114 connects with a drive coupling 121 which is acted upon by a drive spring 120. The drive coupling 121 is in communication with the syringe 122.

Rotation of the trigger 114 about the pivot 115 in a direction R (i.e. downwards into the housing 112 at its first end 114a) causes the second end 114b of the trigger 114 to disengage from the drive coupling 121, thereby letting the drive spring 120 drive the syringe 122 (via the drive coupling 121) along the longitudinal axis 101 and out of an aperture 118 in the housing 112.

The releasable locking mechanism 116 is in communication with sliding sleeve 126 which protrudes, when in a first position, from the aperture 118 in the housing 112. The locking mechanism 116 is deactivated by movement of the sliding sleeve 126 along the longitudinal axis 101 into the housing 112 into a second position.

A first end 126a of the sliding sleeve 126 can be placed against a body into which drug is being delivered, thereby deactivating the releasable locking mechanism 116 and allowing the trigger 114 to rotate in direction R from its rest position to its active position.

Figures 5, 6:
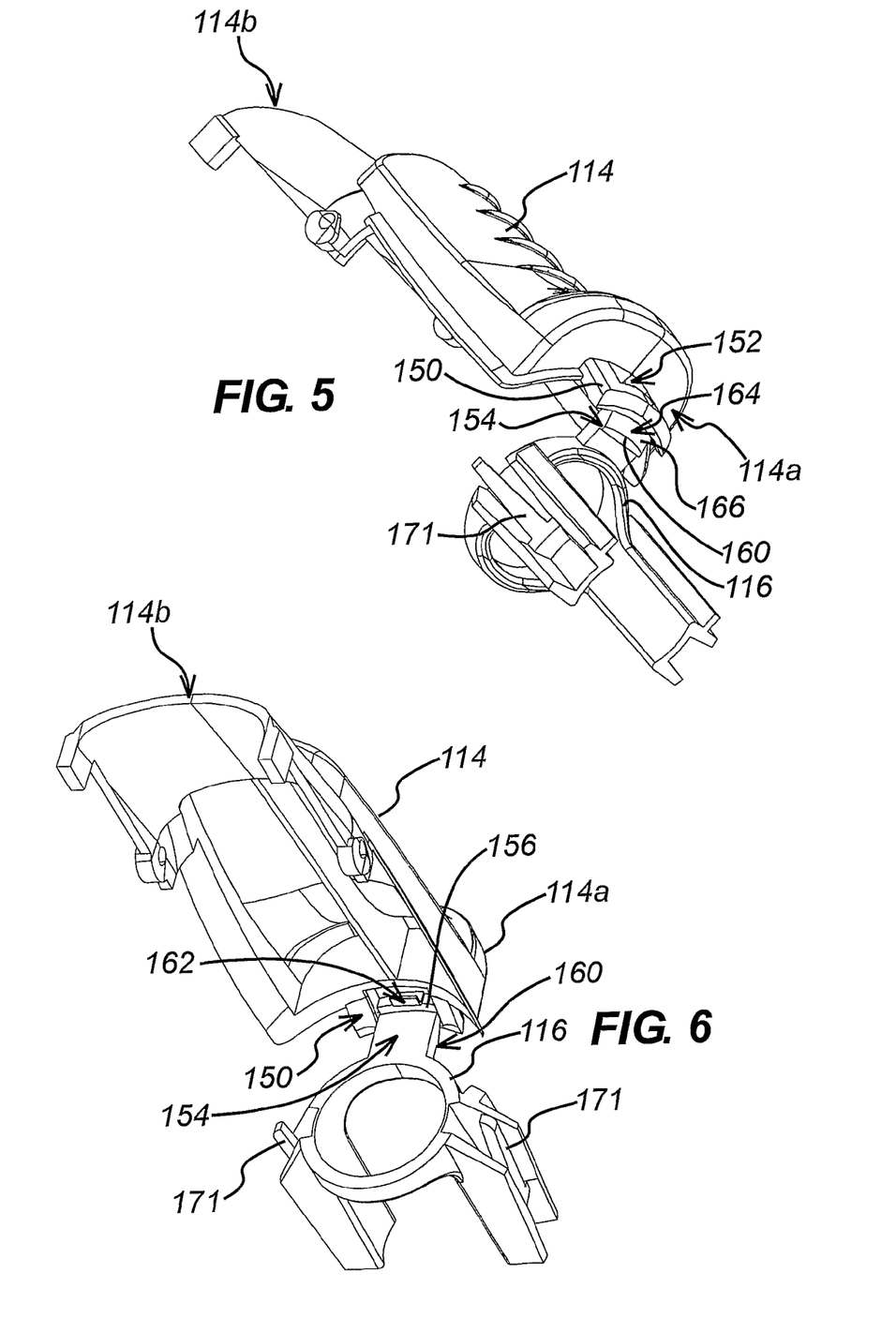
FIG. 5 shows a perspective view of a trigger and releasable locking mechanism according to an embodiment of the present invention.
FIG. 6 shows an alternative perspective view of the trigger and releasable locking mechanism of FIG. 5.

As can be seen from FIGS. 5 and 6, the trigger 114 is provided at its first end 114a with a first portion 150 having a cut-out 152. The first portion 150 extends from the first end 114a of the trigger 114a in a direction substantially parallel to the longitudinal axis 101.

The releasable locking mechanism 116 includes a protrusion 154 which projects in a direction along a perpendicular axis 181 which is perpendicular to the longitudinal axis 101. The cut-out 152 is dimensioned to receive the protrusion 154.

When the releasable locking mechanism 116 is in its first position, an end 154a of the protrusion 154 abuts an under-surface 156 of the first portion 150, thereby preventing rotation of the trigger 114.

When the releasable locking mechanism 116 is in its second position (not shown) following movement of the sliding sleeve 126 into the housing 112, the cut-out 152 is positioned above the end of the protrusion 154 allowing it to pass over the protrusion 154 when a downwards force is applied the trigger 112. Hence, the trigger 112 is no longer prevented from rotating and disengages itself from the drive coupling 121, thereby extending the syringe 122.

The protrusion 154 comprises a first ridge 160. The trigger 114 includes a second portion 162 which extends into the cut-out 152 from the first portion 150 of the trigger 114 and which is arranged to communicate with the second portion 162 following rotation of the trigger 114 so that the first ridge 160 is locked over the second portion 162, thereby preventing movement of the trigger 114 from its active position back to its rest position.

The locking mechanism 116 includes biasing means, in the form of resilient arms 171, which act against the internal surface of the housing 112 to bias the locking mechanism 116 and sliding sleeve 126 in a direction out of aperture 118. This way, following activation of the trigger 112, the first ridge 160 is locked over the second portion 162 of the trigger 112, thereby holding the trigger 112 in its active position.

The first portion 150 of the trigger comprises a second ridge 164 on the under-surface 156 of the first portion 150 which is positioned between the cut-out 152 and the end of the first portion 150. The second ridge 164 abuts the protrusion 154 when force is applied to the trigger 114 in a direction R and the release mechanism is in its first (i.e. engaged) position. This prevents the protrusion 154 from moving into a position in which its end 154a moves over the end of the first portion 150 which would allow the trigger 114 to rotate whilst the releasable locking mechanism 116 was still engaged, thereby accidentally "firing" the injection device 110.

The protrusion 154 has a sloped surface 166 which is angled with respect to the second axis 181 which allows the second portion 162 of the trigger 114 to pass over the protrusion 154 more effectively when the trigger 114 is rotated and the releasable locking mechanism 116 is disengaged.

It will of course be understood that the present invention has been described above purely by way of example and modifications of detail can be made within the scope of the invention.

The invention claimed is:

1. An injection device comprising:
   a housing defining a first axis and adapted to receive a syringe having a discharge nozzle so that the syringe is movable between a retracted position in which the discharge nozzle is contained within the housing and an extended position in which the discharge nozzle extends from the housing through an exit aperture;
   a drive that is acted upon by a drive spring and in turn acts upon the syringe;
   a trigger movable from a rest position, in which it causes the drive to be retained by engaging the drive or drive spring and thereby preventing the drive spring from driving the syringe, to an active position, in which it no longer causes the drive to be so retained by disengaging from the drive or drive spring and thereby permitting the drive spring to drive the syringe via the drive, thus allowing the contents of the syringe to be discharged through the discharge nozzle; and
   a releasable locking mechanism movable from a first position in which the trigger is prevented from moving into its active position to a second position in which the trigger can be moved into its active position,
   wherein the trigger includes a first portion having a cut-out therein, the first portion extending from a first end of the trigger in a direction away from a second end of the trigger substantially parallel to the first axis; and
   the releasable locking mechanism includes a protrusion along a second axis for communicating with the first portion of the trigger when the releasable locking mechanism is in its first position and for communicating with the cut-out when the releasable locking mechanism is in its second position; such that when a force is applied to the trigger when the locking mechanism is in its first position, the first portion of the trigger and the protrusion both flex in such a way that the protrusion is forced away from the cut-out.

2. The injection device of claim 1 wherein the protrusion comprises a ridge adapted to communicate with an edge of the cut-out when the releasable locking mechanism is in its second position and the trigger is in its active position, thereby preventing movement of the trigger from its active position to its rest position.

3. The injection device of claim 2 wherein the trigger further includes a second portion which extends into the cut-out from the first portion of the trigger and which is arranged to communicate with the ridge when the releasable locking mechanism is in its second position and the trigger is in its active position.

4. The injection device of claim 3, wherein the releasable locking mechanism comprises biasing means arranged to bias the protrusion against the second portion.

5. The injection device of claim 1 wherein the first portion of the trigger comprises a ridge positioned on the first portion such that the protrusion is located between the cut-out and the ridge when the trigger is in its rest position such that the ridge communicates with the protrusion if an attempt is made to move the trigger from its rest position.

6. The injection device of claim 1, wherein the protrusion comprises a sloped surface which is angled with respect to the second axis.

7. The injection device of claim 1, wherein the first axis and second axis are perpendicular to each other.

* * * * *